United States Patent
Ueno et al.

(10) Patent No.: US 12,268,539 B2
(45) Date of Patent: Apr. 8, 2025

(54) RADIATION IMAGING APPARATUS, RADIATION IMAGING SYSTEM, CONTROL APPARATUS, CONTROL METHOD, AND NON-TRANSITORY COMPUTER-READABLE STORAGE MEDIUM

(71) Applicant: CANON KABUSHIKI KAISHA, Tokyo (JP)

(72) Inventors: Hiroto Ueno, Kanagawa (JP); Ryosuke Miura, Chiba (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 386 days.

(21) Appl. No.: 17/663,540

(22) Filed: May 16, 2022

(65) Prior Publication Data
US 2022/0370026 A1    Nov. 24, 2022

(30) Foreign Application Priority Data
May 24, 2021  (JP) .................................. 2021-087189

(51) Int. Cl.
*A61B 6/00* (2024.01)
*A61B 6/42* (2024.01)

(52) U.S. Cl.
CPC .......... *A61B 6/4447* (2013.01); *A61B 6/5205* (2013.01); *A61B 6/4233* (2013.01)

(58) Field of Classification Search
CPC .................................................. A61B 6/5205
See application file for complete search history.

(56) References Cited

U.S. PATENT DOCUMENTS

| 5,327,474 A * | 7/1994 | Inoue ..................... A61B 6/032 378/116 |
| 6,243,441 B1* | 6/2001 | Zur ........................ H04N 23/30 378/98.7 |
| 11,243,314 B2 | 2/2022 | Fujiyoshi |
| 11,294,078 B2 | 4/2022 | Miura |
| 11,402,518 B2 | 8/2022 | Ryu |

(Continued)

FOREIGN PATENT DOCUMENTS

JP       2017-127444 A      7/2017

OTHER PUBLICATIONS

U.S. Appl. No. 17/657,435, filed Mar. 31, 2022, Ryosuke Miura.
U.S. Appl. No. 17/808,170, filed Jun. 22, 2022, Takuya Ryu.

*Primary Examiner* — Dani Fox
*Assistant Examiner* — Shun Lee
(74) *Attorney, Agent, or Firm* — VENABLE LLP

(57) ABSTRACT

A radiation imaging apparatus comprising an imaging region configured to acquire a radiation image, a controller configured to set a detection region as a region to be used to detect the radiation in the imaging region and a rotation detector is provided. The rotation detector detects a rotation angle of a reference portion of the imaging region with respect to a reference direction of the subject, and the controller decides, in accordance with a part to be imaged of the subject and the rotation angle, a side located in the same direction as the reference direction of the subject among sides defining an outer edge of the imaging region, sets the detection region at a position away from the side by a predetermined distance for imaging of the part, and controls imaging based on a dose entering the detection region.

20 Claims, 7 Drawing Sheets

(56) References Cited

U.S. PATENT DOCUMENTS

| | | | |
|---|---|---|---|
| 2013/0228694 A1* | 9/2013 | Nakatsugawa | A61B 6/542 250/371 |
| 2014/0177798 A1* | 6/2014 | Kitagawa | A61B 6/56 378/62 |
| 2014/0241504 A1* | 8/2014 | Lundstrom | A61B 6/4458 378/189 |
| 2020/0348424 A1 | 11/2020 | Watanabe | |

* cited by examiner

RADIATION IMAGING APPARATUS, RADIATION IMAGING SYSTEM, CONTROL APPARATUS, CONTROL METHOD, AND NON-TRANSITORY COMPUTER-READABLE STORAGE MEDIUM

BACKGROUND OF THE INVENTION

Field of the Invention

The present invention relates to a radiation imaging apparatus, a radiation imaging system, a control apparatus, a control method, and a non-transitory computer-readable storage medium.

Description of the Related Art

In medical imaging diagnosis or non-destructive inspection, a radiation imaging apparatus using a flat panel detector (FPD) made of a semiconductor material is widely used. Such radiation imaging apparatus is known to monitor radiation entering the radiation imaging apparatus. Japanese Patent Laid-Open No. 2017-127444 describes a radiation imaging apparatus including a rotation detector that detects a direction in which a side 5001 of a radiation imaging apparatus 1001 formed in a rectangular shape exists when viewed from a subject 1011, as shown in FIG. 4. The radiation imaging apparatus 1001 described in Japanese Patent Laid-Open No. 2017-127444 selects, based on the imaging part of the subject and the direction of the radiation imaging apparatus 1001, detected by the rotation detector, when viewed from the subject, a region to be used to detect radiation from a plurality of regions 5005 set for detection of radiation.

SUMMARY OF THE INVENTION

Consider a case in which the radiation imaging apparatus 1001 is fixed to a platform (gantry) 5004 or the like to perform imaging in the standing position, as shown in FIG. 4. In this case, when viewed from the subject 1011, four states including the first state in which the side 5001 of the radiation imaging apparatus 1001 is a left side, the second state obtained by rotating the radiation imaging apparatus 1001 by 90° counterclockwise with respect to the first state, the third state obtained by further rotating the radiation imaging apparatus 1001 by 90° counterclockwise with respect to the second state, and the fourth state obtained by rotating the radiation imaging apparatus 1001 by 90° counterclockwise with respect to the third state are considered. At this time, as shown in FIG. 4, the distance from a side 5011 on the side of the head of the subject 1011 in imaging in the standing position by the radiation imaging apparatus 1001 to a region closest to the side 5011 among the plurality of regions (detection areas 5005) for detection of radiation can be different between the first and second states. Similarly, the distance from the side 5011 on the side of the head of the subject 1011 in imaging in the standing position by the radiation imaging apparatus 1001 to the region closest to the side 5011 among the plurality of regions for detection of radiation can be different between the first and fourth states and between the third and fourth states. If the subject is arranged in accordance with the radiation imaging apparatus 1001 fixed to the platform (gantry) 5004 in the direction in the second state while the radiation imaging apparatus 1001 is fixed to the platform (gantry) 5004 in the first state, the region used to detect radiation irradiation may deviate from the target part of the subject. If the position of the region for detection of radiation irradiation deviates from the position of the target part of the subject, the detection accuracy of radiation irradiation may degrade.

Some embodiments of the present invention provide a technique advantageous for a radiation imaging apparatus to properly detect radiation irradiation on an imaging region regardless of the rotation angle of the imaging region with respect to a subject.

According to some embodiments, a radiation imaging apparatus comprising an imaging region in which a plurality of pixels configured to generate signals to acquire a radiation image corresponding to incident radiation are arranged, a controller configured to set a detection region as a region to be used to detect the radiation in addition to acquisition of the radiation image in the imaging region, and a rotation detector, wherein when the imaging region is arranged to face a subject, the rotation detector is configured to detect a rotation angle of a reference portion of the imaging region about an axis in a normal direction of the imaging region with respect to a reference direction of the subject, and the controller is configured to decide, in accordance with a part to be imaged of the subject and the rotation angle, a side located in the same direction as the reference direction of the subject among a plurality of sides defining an outer edge of the imaging region, set the detection region at a position away from the side by a predetermined distance for imaging of the part to be imaged, and control imaging based on a dose of the radiation entering the detection region, is provided.

According to some other embodiments, a control apparatus for controlling a radiation imaging apparatus comprising an imaging region in which a plurality of pixels configured to generate signals to acquire a radiation image corresponding to incident radiation are arranged and a rotation detector, and a radiation generation apparatus configured to irradiate the radiation imaging apparatus with the radiation, wherein when the imaging region is arranged to face a subject, the rotation detector is configured to detect a rotation angle of a reference portion of the imaging region about an axis in a normal direction of the imaging region with respect to a reference direction of the subject, and the control apparatus is configured to control the radiation generation apparatus based on a dose of the radiation detected in a detection region as a region to be used to detect the radiation in addition to acquisition of the radiation image in the imaging region, and decide, in accordance with a part to be imaged of the subject and the rotation angle, a side located in the same direction as the reference direction of the subject among a plurality of sides defining an outer edge of the imaging region, thereby setting the detection region at a position away from the side by a predetermined distance for imaging of the part to be imaged, is provided.

According to still other embodiments, a control method of a radiation imaging apparatus comprising an imaging region in which a plurality of pixels configured to generate signals to acquire a radiation image corresponding to incident radiation are arranged, and a rotation detector, the method comprising: arranging the imaging region to face a subject; causing the rotation detector to detect a rotation angle of a reference portion of the imaging region about an axis in a normal direction of the imaging region with respect to a reference direction of the subject; setting a detection region as a region to be used to detect the radiation in addition to acquisition of the radiation image in the imaging region; and controlling imaging based on a dose of the radiation entering the detection region, wherein in accordance with a part to be imaged of the subject and the rotation angle, a side located in the same direction as the reference direction of the subject is decided among a plurality of sides defining an outer edge of the imaging region, and the detection region is set at a position away from the side by a predetermined distance for imaging of the part to be imaged, is provided.

According to yet other embodiments, a non-transitory computer-readable storage medium storing a program for causing a computer to execute a control method of a radiation imaging apparatus comprising an imaging region in which a plurality of pixels configured to generate signals to acquire a radiation image corresponding to incident radiation are arranged, and a rotation detector, the method comprising: arranging the imaging region to face a subject; causing the rotation detector to detect a rotation angle of a reference portion of the imaging region about an axis in a normal direction of the imaging region with respect to a reference direction of the subject; setting a detection region as a region to be used to detect the radiation in addition to acquisition of the radiation image in the imaging region; and controlling imaging based on a dose of the radiation entering the detection region, wherein in accordance with a part to be imaged of the subject and the rotation angle, a side located in the same direction as the reference direction of the subject is decided among a plurality of sides defining an outer edge of the imaging region, and the detection region is set at a position away from the side by a predetermined distance for imaging of the part to be imaged, is provided.

Further features of the present invention will become apparent from the following description of exemplary embodiments (with reference to the attached drawings).

DESCRIPTION OF THE EMBODIMENTS

Figure 1:
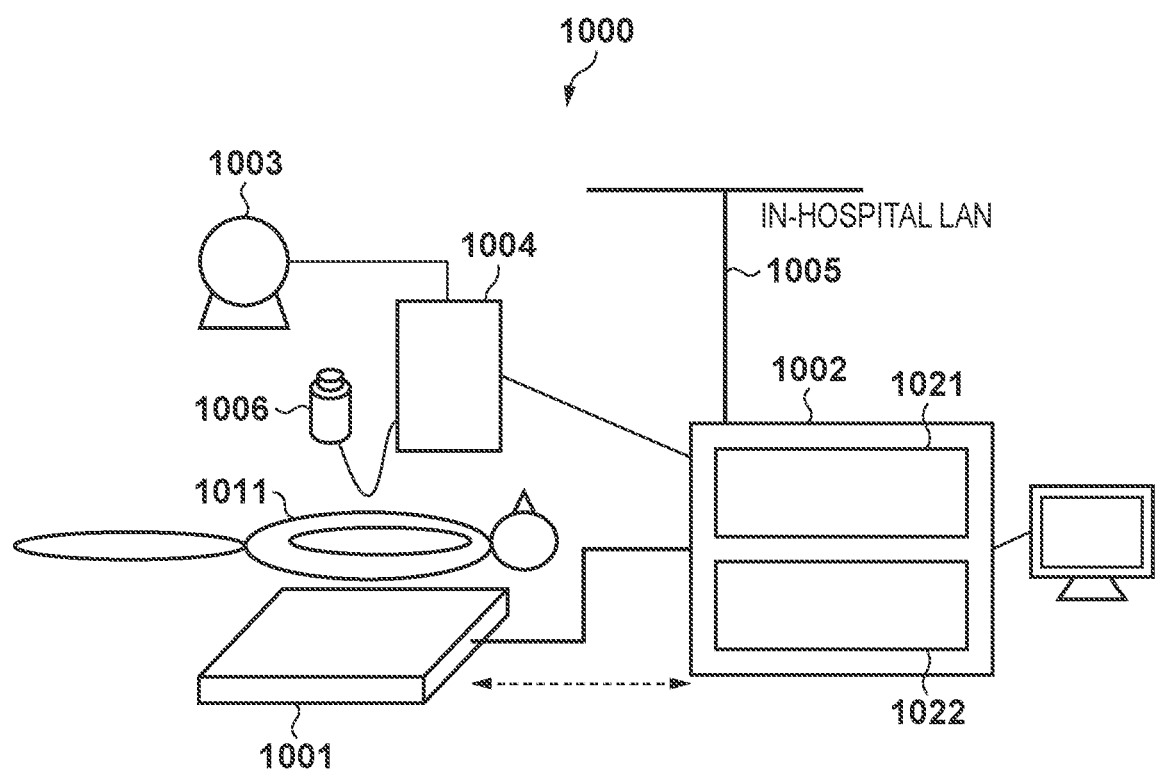
FIG. 1 is a view showing an example of the arrangement of a radiation imaging system using a radiation imaging apparatus according to an embodiment.

Hereinafter, embodiments will be described in detail with reference to the attached drawings. Note, the following embodiments are not intended to limit the scope of the claimed invention. Multiple features are described in the embodiments, but limitation is not made to an invention that requires all such features, and multiple such features may be combined as appropriate. Furthermore, in the attached drawings, the same reference numerals are given to the same or similar configurations, and redundant description thereof is omitted.

Radiation according to the present invention can include not only α-rays, β-rays, and γ-rays that are beams generated by particles (including photons) emitted by radioactive decay but also beams having equal or more energy, for example, X-rays, particle rays, and cosmic rays.

The arrangements and operations of a radiation imaging apparatus and a radiation imaging system according to an embodiment will be described with reference to FIGS. 1 to 8. FIG. 1 shows an example of the arrangement of a radiation imaging system 1000 using a radiation imaging apparatus 1001 according to this embodiment. For example, the radiation imaging system 1000 can be used to capture a radiation image in a hospital. The radiation imaging system 1000 includes the radiation imaging apparatus 1001, a control apparatus 1002, a radiation source 1003, a radiation generation apparatus 1004, an in-hospital LAN 1005, and an irradiation switch 1006.

The radiation imaging apparatus 1001 detects radiation having passed through a subject 1011 as a patient or object, thereby generating a signal for forming an image. The control apparatus 1002 is communicably connected to the radiation imaging apparatus 1001 and the radiation generation apparatus 1004. The control apparatus 1002 can perform, for example, setting of an imaging condition, operation control, and the like for the radiation imaging apparatus 1001. For example, the radiation imaging apparatus 1001 can perform, for example, transfer of an image signal, transmission of information of the dose of incident radiation, transmission of a signal for performing automatic exposure control (AEC), and the like for the control apparatus 1002. In this embodiment, the control apparatus 1002 includes, as an input device that allows setting of an imaging condition, operation control, and input of information such as image information, for example, a mouse and a keyboard, and also includes a display as an output device. Furthermore, the control apparatus 1002 can perform control of radiation irradiation for the radiation generation apparatus 1004 that generates radiation from the radiation source 1003. The control apparatus 1002 can be an apparatus for controlling the radiation imaging apparatus 1001 and the radiation generation apparatus 1004 for irradiating the radiation imaging apparatus 1001 with radiation.

To generate radiation, the radiation source 1003 includes, for example, a rotor and a radiation tube (X-ray tube) that accelerates electrons by a high voltage and collides them against an anode. An ON operation of the irradiation switch 1006 such as the pressing of the switch by the user requests the control apparatus 1002 to apply radiation.

The control apparatus 1002 includes a communication controller 1021 that controls communication, and a controller 1022 that performs operation control, dose control, and the like. The communication controller 1021 may be configured as a unit different from the control apparatus 1002. The controller 1022 monitors the states of the radiation imaging apparatus 1001 and the radiation generation apparatus 1004, and controls radiation irradiation and imaging. The subject is irradiated with the radiation emitted from the radiation source 1003. The radiation imaging apparatus 1001 detects the radiation having been emitted from the radiation source 1003 and having passed through the subject, thereby generating a signal for forming an image.

The radiation imaging apparatus 1001 includes a wireless communicator and a wired communicator (none are shown), and can communicate with the communication controller 1021 of the control apparatus 1002. The wired communicator allows exchange of information with the communication controller 1021 of the control apparatus 1002 by cable connection complying with a known communication standard. Furthermore, the wireless communicator includes, for example, a circuit substrate including a communication IC. The circuit substrate including the communication IC is electrically connected to an antenna (not shown), and the antenna transmits/receives a wireless radio wave. The circuit substrate including the communication IC performs communication processing of a protocol based on a wireless LAN via the antenna. The wireless communication frequency band, standard, and method in wireless communication are not particularly limited, and a known method such as a short-range wireless method or a UWB method is used. In addition, the wireless communicator has a plurality of wireless communication methods, and may select an appropriate method to perform communication. The arrangement may be such that only one of the wired communicator and the wireless communicator is arranged. Any arrangement may be adopted as long as the radiation imaging apparatus 1001 and the control apparatus 1002 can communicate with each other.

Between the control apparatus 1002 and the radiation imaging apparatus 1001, setting of an imaging condition, operation control, transfer of an image signal, and exchange of the arrival dose of radiation entering the radiation imaging apparatus 1001, an AEC signal, and the like are performed. Furthermore, dose information, an irradiation control signal, and the like are exchanged between the control apparatus 1002 and the radiation generation apparatus 1004. The dose information indicates the dose of radiation emitted from the radiation source 1003. The arrival dose indicates the dose of radiation, arrived at the radiation imaging apparatus 1001, of the radiation emitted from the radiation source 1003.

Figure 2:
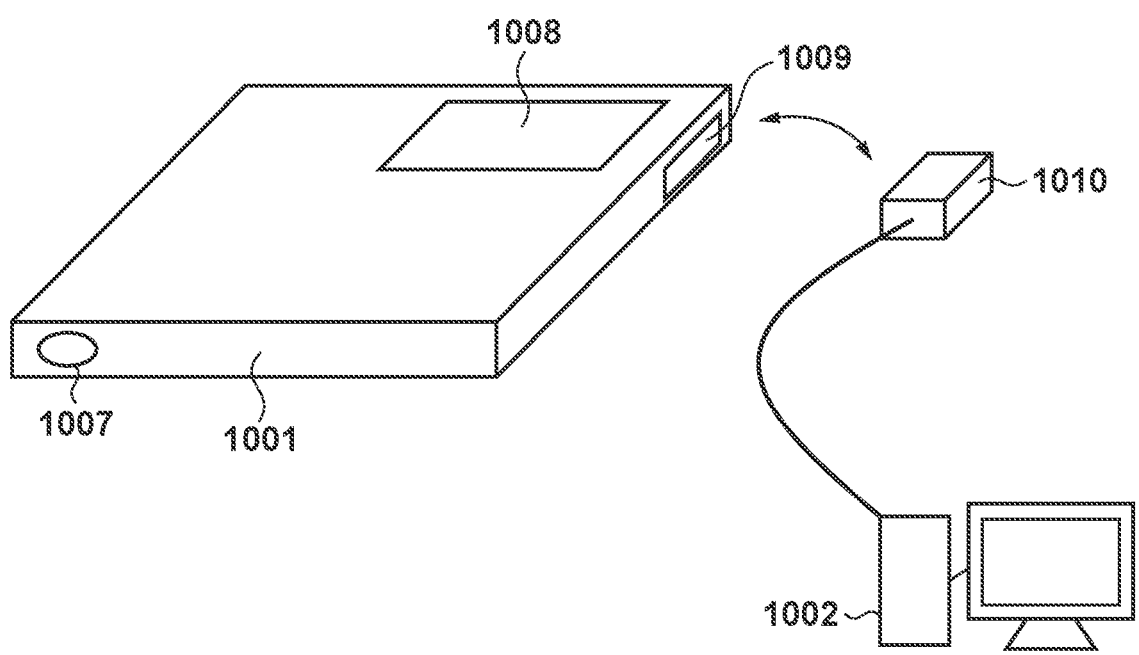
FIG. 2 is a view showing an example of the outer appearance of the radiation imaging apparatus shown in FIG. 1.

The radiation imaging apparatus 1001 can be, for example, a portable cassette flat panel detector. FIG. 2 shows the outer appearance of the radiation imaging apparatus 1001 according to the embodiment. The radiation imaging apparatus 1001 includes a power button 1007 for turning on/off the power supply, a battery unit 1008 for supplying power, and a connector 1009. For example, the battery unit 1008 is detachable, and the battery main body is chargeable by a battery charger. The radiation imaging apparatus 1001 may be connected to the control apparatus 1002 via a sensor cable 1010. In this case, one end of the sensor cable 1010 is connected to the radiation imaging apparatus 1001 via the connector 1009. When the radiation imaging apparatus 1001 and the control apparatus 1002 are connected via the sensor cable 1010, communication between the radiation imaging apparatus 1001 and the control apparatus 1002 is switched to wired communication automatically or by a user operation, and information is exchanged between these apparatuses by the wired communication. As described above, in this embodiment, the radiation imaging apparatus 1001 and the control apparatus 1002 have separate arrangements. However, the present invention is not limited to this. The radiation imaging apparatus 1001 may have an integrated arrangement including a controller having the function of the control apparatus 1002. If the radiation imaging apparatus 1001 includes the function of the control apparatus 1002, the controller of the radiation imaging apparatus 1001 may be formed by, for example, an ASIC or the like.

Figure 3:
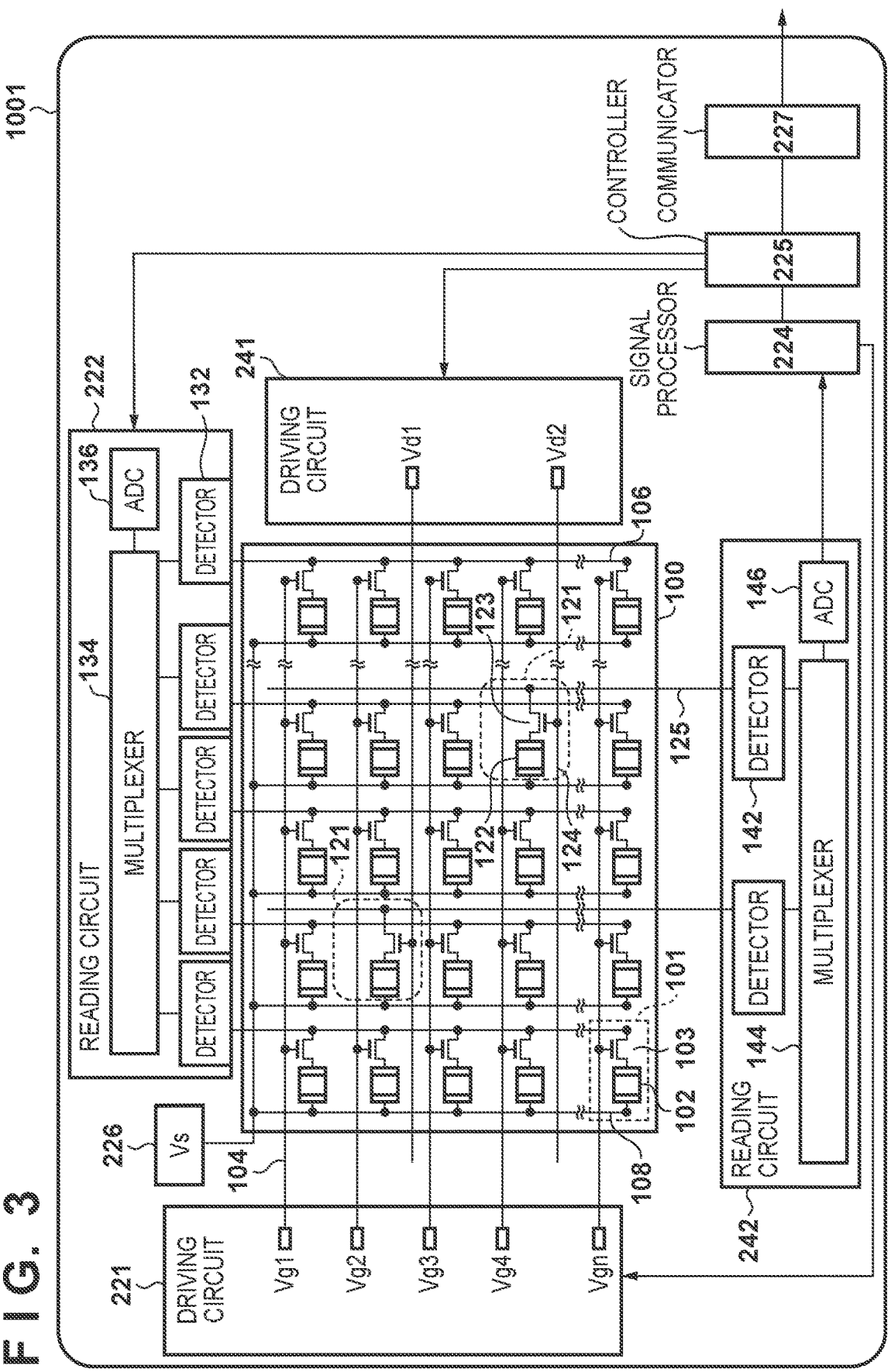
FIG. 3 is a circuit diagram showing an example of the circuit arrangement of the radiation imaging apparatus shown in FIG. 1.

FIG. 3 shows an example of the internal arrangement of the radiation imaging apparatus 1001 according to this embodiment. The radiation imaging apparatus 1001 includes a plurality of pixels 101 that are arrayed in a matrix in an imaging region 100 so as to form a plurality of rows and a plurality of columns and generate signals corresponding to incident radiation. The plurality of pixels 101 are arranged to generate signals to acquire a radiation image. In the imaging region 100, detection elements 121 each for detecting radiation entering the imaging region 100 are arrayed. Each pixel 101 includes a conversion element 102 that converts radiation into an electrical signal, and a switch 103 arranged between the corresponding column signal line 106 and the corresponding conversion element 102. Each detection element 121 includes a conversion element 122 that converts radiation into an electrical signal and a switch 123 arranged between a corresponding detection signal line 125 and the corresponding conversion element 122. In this embodiment, as shown in FIG. 3, in addition to the plurality of pixels 101 for forming a radiation image, the plurality of detection elements 121 each for detecting radiation entering the imaging region 100 are arrayed. For example, a signal output from each detection element 121 need not be used as a signal representing the luminance of a pixel at the position, in the radiation image, where the detection element 121 is arranged. The present invention, however, is not limited to this. The detection elements 121 need not be arranged in addition to the pixels 101, and a part of the plurality of pixels 101 may function as the detection elements 121.

Each of the conversion elements 102 and 122 can be formed from a scintillator that converts radiation into light and a photoelectric conversion element that converts the light into an electrical signal. The scintillator is generally made in the form of a sheet so as to cover the imaging region 100 and can be shared by the plurality of pixels 101 and the plurality of detection elements 121. Each of the conversion elements 102 and 122 may be formed from a conversion element that directly converts radiation into an electrical signal. Each of the switches 103 and 123 can include, for example, a thin film transistor (TFT) in which an active region is formed by a semiconductor such as amorphous silicon or polysilicon.

The radiation imaging apparatus 1001 includes the plurality of column signal lines 106 and a plurality of driving lines 104. Each of the plurality of column signal lines 106 corresponds to one of the plurality of columns in the imaging region 100. Each of the plurality of driving lines 104 corresponds to one of the plurality of rows in the imaging region 100. Each of the plurality of driving lines 104 is driven by a driving circuit 221.

One of the two electrodes of each conversion element 102 is connected to one of the two main electrodes of the corresponding switch 103, and the other electrode of each conversion element 102 is connected to a corresponding bias line 108. As shown in FIG. 3, each bias line 108 extends in the column direction and is commonly connected to the plurality of conversion elements 102 arrayed in the column direction. Each bias line 108 receives a bias voltage Vs from a power supply unit 226, and supplies it to each conversion element 102. The other main electrodes of the switches 103 of the plurality of pixels 101 forming one column are connected to one of the plurality of column signal lines 106. The control electrodes of the switches 103 of the plurality of imaging pixels 101 forming one row are connected to one of the plurality of driving lines 104.

The plurality of column signal lines 106 are connected to a reading circuit 222. The reading circuit 222 can include a plurality of detectors 132, a multiplexer 134, and an AD converter 136. Each of the plurality of column signal lines 106 is connected to a corresponding one of the plurality of detectors 132 of the reading circuit 222. In this embodiment, one column signal line 106 corresponds to one detector 132. Each detector 132 includes, for example, a differential amplifier. The multiplexer 134 selects the plurality of detectors 132 in a predetermined order, and supplies, to the AD converter 136, a signal output from the selected detector 132. The AD converter 136 converts the supplied analog signal into a digital signal and outputs the digital signal.

One of the two electrodes of each conversion element 122 is connected to one of the two main electrodes of the corresponding switch 123, and the other electrode of each conversion element 122 is connected to the corresponding bias line 108. The other main electrode of each switch 123 is electrically connected to the corresponding detection signal line 125. The control electrode of each switch 123 is electrically connected to a corresponding driving line 124. The radiation imaging apparatus 1001 can include the plurality of detection signal lines 125. One detection signal line 125 can be connected to one or more detection elements 121. The driving line 124 is driven by a driving circuit 241. One or more detection elements 121 can be connected to one drive line 124.

Each detection signal line 125 is connected to a reading circuit 242. The reading circuit 242 can include a plurality of detectors 142, a multiplexer 144, and an AD converter 146. Each of the plurality of detection signal lines 125 can be connected to a corresponding one of the plurality of detectors 142 of the reading circuit 242. In this embodiment, one detection signal line 125 corresponds to one detector 142. Each detector 142 includes, for example, a differential amplifier. The multiplexer 144 selects the plurality of detectors 142 in a predetermined order, and supplies, to the AD converter 146, a signal output from the selected detector 142. The AD converter 146 converts the supplied analog signal into a digital signal and outputs the digital signal.

The output from the reading circuit 242 (AD converter 146) is supplied to a signal processor 224 and processed by the signal processor 224. Based on the output from the reading circuit 242 (AD converter 146), the signal processor 224 outputs information indicating radiation irradiation on the radiation imaging apparatus 1001. More specifically, the signal processor 224 may detect the presence/absence of radiation irradiation on the radiation imaging apparatus 1001, and calculate at least one of the radiation irradiation amount (dose) and the integrated irradiation amount (the integration value of the dose). Based on information from the signal processor 224, a controller 225 controls the driving circuits 221 and 241 and the reading circuit 242. Based on the information from the signal processor 224, the controller 225 controls, for example, the start and end of exposure (accumulation of charges corresponding to the emitted radiation by the pixels 101). A communicator 227 communicates with the control apparatus 1002. The communicator 227 may include two communicators of a wired communicator and a wireless communicator for performing communication with the control apparatus 1002. As described above, in this embodiment, the detection elements 121 are arrayed independently of the pixels 101. However, the pixel 101 and the detection element 121 may have the same structure, and may be controlled using the same driving circuit and reading circuit.

Figure 4:
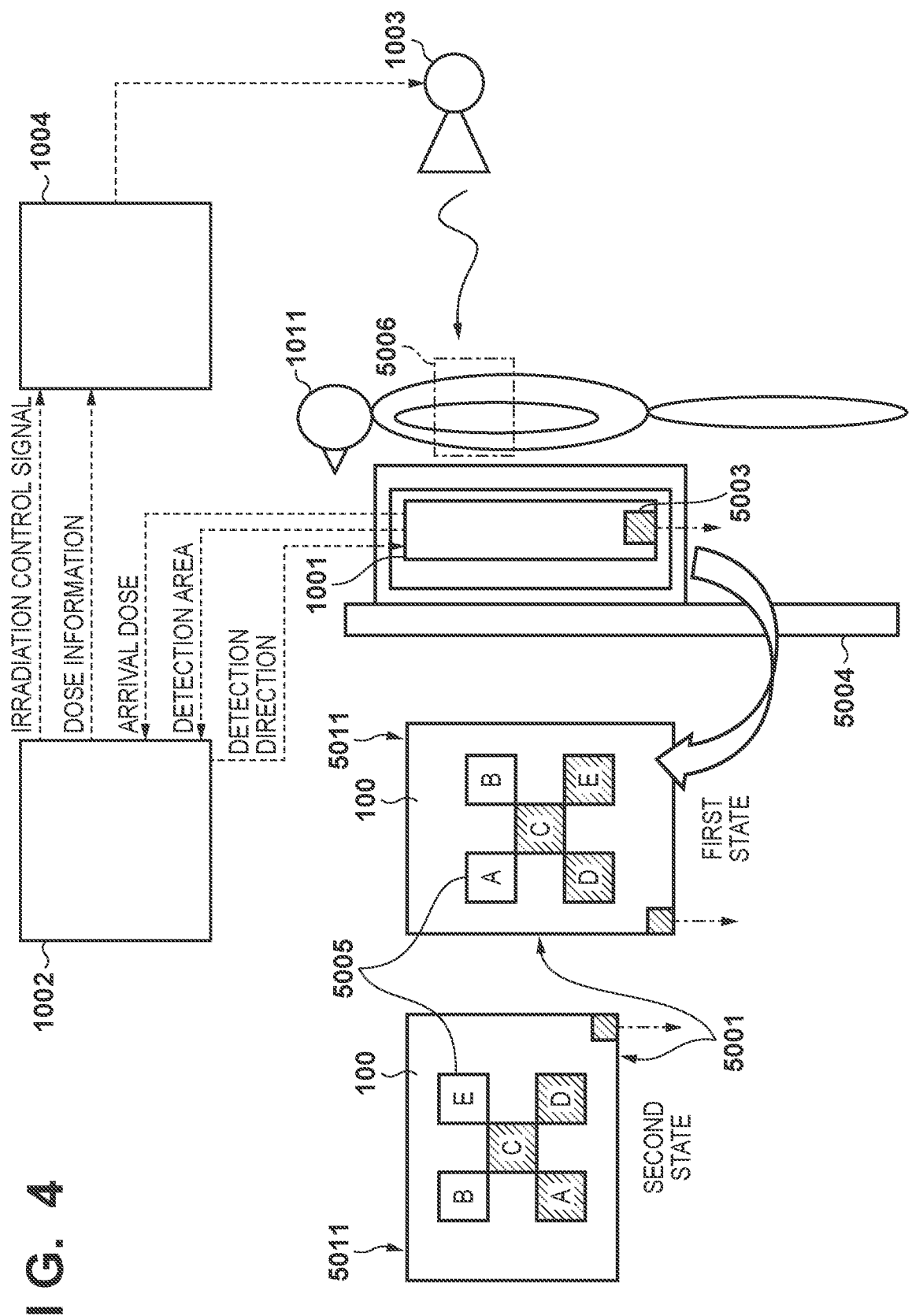
FIG. 4 is a view for explaining imaging in the standing position using the radiation imaging system shown in FIG. 1.

Rotation of the imaging region 100 of the radiation imaging apparatus 1001 with respect to the reference direction of the subject will be described next by exemplifying a case in which imaging in the standing position is performed. When performing imaging of the subject in the standing position, the radiation imaging apparatus 1001 is installed to be erected by being fixed to a platform (gantry) 5004 or the like. FIG. 4 shows an example of the arrangement of the radiation imaging system 1000 when performing imaging of subject 1011 in the standing position. For example, the radiation imaging apparatus 1001 can be installed in the platform (gantry) 5004 in four directions. One is the first state in which a side 5001 of the radiation imaging apparatus 1001 is the left side when viewed from the subject 1011. Another one is the second state in which the 5001 of the radiation imaging apparatus 1001 is the bottom side by rotating the radiation imaging apparatus 1001 by 90° counterclockwise with respect to the first state. Similarly, although not shown in FIG. 4, in the third state in which the side 5001 is the right side by further rotating the radiation imaging apparatus 1001 by 90° counterclockwise with respect to the second state, or in the fourth state in which the side 5001 is the upper side by rotating the radiation imaging apparatus 1001 by 90° counterclockwise with respect to the third state, the radiation imaging apparatus 1001 can be installed in the platform (gantry) 5004.

In the imaging region 100 of the radiation imaging apparatus 1001, a plurality of detection areas 5005 each including the detection element 121 and used to detect incident radiation are preset. The number of detection areas 5005 and their arrangement are not limited but each of the plurality of detection areas 5005 may correspond to each assumed part to be imaged. For the sake of descriptive simplicity, assume that five detection areas 5005 are preset, as shown in FIG. 4. In the first state shown in FIG. 4, as the five detection areas 5005, a detection area A located at the upper left position, a detection area B located at the upper right position, a detection area C located at the center, a detection area D located at the lower left position, and a detection area E located at the lower right position are set when viewed from the subject 1011. When indicating a specific detection area, reference symbols A to E are added like "detection area A"; otherwise, "detection area 5005" is described.

In each detection area 5005, incident radiation is detected, and for example, the radiation imaging apparatus 1001 (radiation imaging system 1000) executes control such as AEC. The controller 225 of the radiation imaging apparatus 1001 or the control apparatus 1002 may control the radiation generation apparatus 1004 based on the dose of the radiation detected in the radiation detection area 5005 in the imaging region 100. For example, based on the arrival dose detected in each detection area 5005, the control apparatus 1002 can control the radiation generation apparatus 1004 so as to prevent excessive radiation irradiation from the radiation source 1003. However, the proper arrival dose is different for each part to be imaged of the subject 1011. When the direction of the radiation imaging apparatus 1001 is the direction in each of the first to fourth states, the position of the detection area 5005 for the part to be imaged of the subject 1011 positioned with respect to the platform (gantry) 5004 can change. To cope with this, the radiation imaging apparatus 1001 according to this embodiment includes a rotation detector 5003 that detects, when the imaging region 100 is arranged to face the subject 1011, the rotation angle of the reference portion of the imaging region 100 about the axis in the normal direction of the imaging region 100 with respect to the reference direction of the subject 1011. The controller 225 of the radiation imaging apparatus 1001 sets the radiation detection region in the imaging region 100 in accordance with a part 5006 to be imaged of the subject 1011 and the rotation angle detected by the rotation detector 5003. For example, the controller 225 selects an appropriate detection area (for example, the detection area A) from the above-described plurality of detection areas 5005, and adjusts the position of the selected detection area A, thereby setting the radiation detection region. This suppresses the possibility that the detection region as a region to be used to detect radiation irradiation in addition to acquisition of a radiation image deviates from the target part of the subject 1011. That is, it is possible to acquire a radiation image using the proper dose by suppressing extra radiation irradiation or insufficient radiation irradiation from the radiation source 1003.

A case in which a chest is imaged as the part 5006 to be imaged of the subject 1011 in imaging in the standing position, as shown in FIG. 4, will be described in this specification. Thus, a direction toward the head of the subject 1011 is set as the reference direction of the subject 1011 serving as the reference of rotation of the imaging region 100 of the radiation imaging apparatus 1001. Furthermore, the side 5001 serving as the left side when viewed from the subject 1011 in the above-described first state is set as the reference portion for obtaining the rotation angle of the imaging region 100 of the radiation imaging apparatus 1001 with respect to the reference direction of the subject 1011. The present invention, however, is not limited to this, and the embodiment to be described below is also applicable to imaging in the supine position and another part to be imaged, such as a head, an abdominal part, or a placenta. That is, the function of each of the radiation imaging apparatus 1001 and the radiation imaging system 1000 described in this embodiment can be implemented by appropriately setting the reference portion of the radiation imaging apparatus 1001 and the reference direction of the subject 1011 in accordance with the part to be imaged and positioning of the subject 1011 when performing imaging using the radiation imaging apparatus 1001. Furthermore, as described above, the radiation imaging apparatus 1001 can be installed in the platform (gantry) 5004 in the four states including the first to fourth states. However, a description will be provided by focusing on the first and second states.

As shown in FIG. 4, the radiation imaging apparatus 1001 is fixed to the platform (gantry) 5004 to be aligned with the position of the part 5006 to be imaged of the subject 1011. Furthermore, the radiation imaging apparatus 1001 includes the imaging region 100 in which the above-described five detection areas 5005 are preset as radiation detection regions. The radiation imaging apparatus 1001 also includes the rotation detector 5003 for detecting the rotation angle of the reference portion (the side 5001 in this embodiment) of the imaging region 100 about the axis in the normal direction of the imaging region 100 with respect to the reference direction (the direction toward the head in this embodiment) of the subject 1011.

The rotation detector 5003 may detect the rotation angle of the side 5001 as the reference portion by detecting the direction of the side 5001 as the reference portion with respect to the vertical direction. In this case, for example, the rotation detector 5003 may be an acceleration sensor that detects the acceleration in the gravity direction. If the rotation detector 5003 includes a 1-axis acceleration sensor, the acceleration sensor may be installed so that, for example, the output is large in the first state and is small in the second state. Alternatively, if, for example, the rotation detector 5003 includes a 2-axis acceleration sensor, the acceleration sensor may be installed so that, for example, the output is large with respect to the first axis in the first state and is large with respect to the second axis in the second state. Alternatively, the rotation detector 5003 may include a 3-axis acceleration sensor.

Furthermore, the rotation detector 5003 may detect the rotation angle of the side 5001 as the reference portion by detecting a detection object fixed to the platform (gantry) 5004 to which the radiation imaging apparatus 1001 is attached. In this case, the detection object may be a convex object (for example, a projection) arranged at a predetermined position of the platform (gantry) 5004. When the rotation detector 5003 includes a pressure sensor that detects a pressure applied by the projection arranged as the detection object, it can detect the rotation angle of the side 5001 as the reference portion. Similarly, the rotation detector 5003 may have a convex shape, and a concave portion may be provided as the detection object at the predetermined position of the platform (gantry) 5004. Furthermore, for example, a magnetic material such as a magnet may be arranged as the detection object on the platform (gantry) 5004, and the rotation detector 5003 may be a magnetic sensor. When the radiation imaging apparatus 1001 is set on the platform (gantry) 5004, the magnetic sensor as the rotation detector 5003 detects the magnetic material arranged at the predetermined position of the platform (gantry) 5004, thereby detecting the rotation angle of the side 5001 as the reference portion.

As described above, when the imaging region 100 is arranged to face the subject 1011, the rotation detector 5003 can detect the rotation angle of the reference portion of the imaging region 100 about the axis in the normal direction of the imaging region 100 with respect to the reference direction of the subject 1011. The radiation imaging apparatus 1001 outputs, to the controller 225, information of the rotation angle detected by the rotation detector 5003, and the controller 225 generates information of the detection area 5005 to be used (designation information of enabling/disabling of each detection area). A case in which the controller 225 of the radiation imaging apparatus 1001 sets the detection area 5005 will now be described. However, these control operations may be performed by the control apparatus 1002. The following description assumes that control to be described below is similarly executed by the controller 225 but control may be executed by the control apparatus 1002. After setting the detection area 5005 to be used as a radiation detection region, the controller 225 of the radiation imaging apparatus 1001 controls imaging in accordance with the dose of incident radiation based on the information of the detection area 5005 to be used as a detection region. For example, the controller 225 outputs, to the control apparatus 1002, information of the arrival dose in the detection area 5005 to be used as a detection region.

Figure 5:
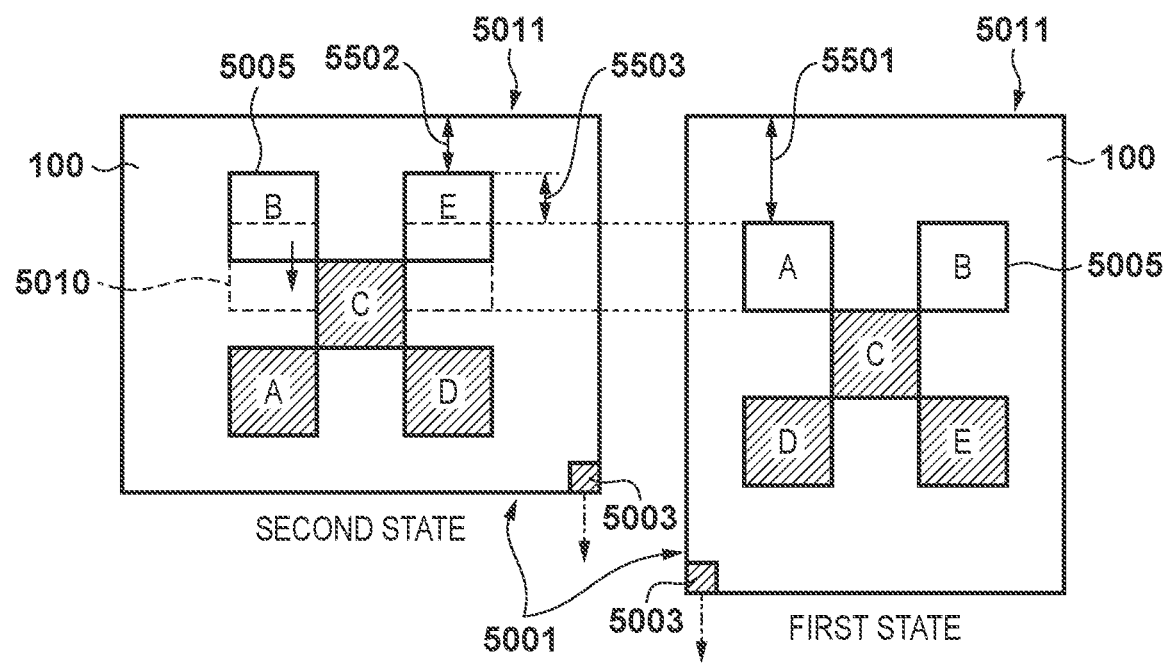
FIG. 5 is a view for explaining a method of setting a detection region of the radiation imaging apparatus shown in FIG. 1.

FIG. 5 is a view focusing on the imaging region 100 in the example of the arrangement of the radiation imaging system 1000 shown in FIG. 4. FIG. 5 shows the positions of the detection areas 5005 preset in the imaging region 100 when the radiation imaging apparatus 1001 is stored in the platform (gantry) 5004 in the first and second states in imaging in the standing position. In the first state, the detection areas A and B to be used as the detection regions in imaging of the chest are at a position of a distance 5501 from a side 5011 (in this case, the upper side) located in the same direction as the direction toward the head, which is the reference direction of the subject 1011, among the plurality of sides defining the outer edge of the imaging region 100. Similarly, in the second state, the detection areas B and E to be used as the detection regions in imaging of the chest are at a position of a distance 5502 from the side 5011 (upper side)

located in the same direction as the direction toward the head, which is the reference direction of the subject 1011, among the plurality of sides defining the outer edge of the imaging region 100.

As described above, the position of the detection area 5005 to be used as the radiation detection region when imaging the chest in the standing position may be different between the first and second states. In the case shown in FIG. 5, the distance from the side 5011 to the detection areas A and B to be used as the detection regions in the first state and the distance from the side 5011 to the detection areas B and E to be used as the detection regions in the second state are different from each other by a distance 5503. That is, when the radiation imaging apparatus 1001 is fixed to the platform (gantry) 5004 in the first state, if the subject 1011 is aligned with the radiation imaging apparatus 1001 fixed to the platform (gantry) 5004 in the direction in the second state, the detection areas 5005 to be used as the radiation detection regions may deviate from the target part of the subject 1011. For example, when imaging the chest, the jaw of the subject 1011 may be aligned with the upper portion of the platform (gantry) 5004. Therefore, the distance from the upper portion of the platform (gantry) 5004 to the chest is substantially constant. On the other hand, if the radiation imaging apparatus 1001 is stored in the platform (gantry) 5004 to coincide with the upper portion, the distance from the upper portion of the platform (gantry) 5004 to the detection areas A and B in the first state and the distance from the upper portion of the platform (gantry) 5004 to the detection areas B and E in the second state are different from each other by the distance 5503. If the positional relationship between the radiation detection regions and the target part of the subject 1011 deviates, the accuracy of control such as AEC performed by detecting radiation irradiation may degrade.

To cope with this, in this embodiment, the controller 225 (or the control apparatus 1002) of the radiation imaging apparatus 1001 decides the side 5011 located in the same direction as the reference direction of the subject 1011, among the plurality of sides defining the outer edge of the imaging region 100, in accordance with the part 5006 to be imaged of the subject 1011 and the rotation angle detected by the rotation detector 5003. In this embodiment, the part 5006 to be imaged of the subject is the chest. Therefore, based on the information of the rotation angle of the side 5001 as the reference portion of the imaging region 100 detected by the rotation detector 5003, the controller 225 can decide the side 5011 corresponding to the upper side as the direction toward the head as the reference direction of the subject 1011.

Next, the controller 225 sets the detection region at a position away from the side 5011 by a predetermined distance (for example, the distance 5501) for imaging of the part 5006 to be imaged. More specifically, based on the rotation angle detected by the rotation detector 5003, the controller 225 selects the detection area 5005 to be used as the detection region from the plurality of detection areas 5005 in accordance with the part 5006 to be imaged and the rotation angle. In the case of imaging of the chest or the like, for example, the controller 225 may select, as the detection area to be used as the detection region, from the plurality of detection areas 5005, the detection area 5005 closest to the side 5011 corresponding to the upper side when viewed from the subject 1011. Next, the controller 225 adjusts the position of the selected detection area 5005 so that the position of the selected detection area 5005 is away from the side 5011 by the predetermined distance.

In the first state, the controller 225 selects the detection areas A and B as the detection areas 5005 to be used as the detection regions, the detection areas A and B are away from the side 5011 by the predetermined distance 5501 for imaging of the chest, and thus the position need not be adjusted. In the second state, the controller 225 selects the detection areas B and E as the detection areas 5005 to be used as the detection regions. Next, the detection areas B and E are at a position away from the side 5011 not by the predetermined distance 5501 but by the distance 5502 for imaging of the chest. Therefore, the controller 225 adjusts the positions of the detection areas B and E to be used as the detection regions to a position 5010 away from the side 5011 as the upper side in the second state by the distance 5501. This embodiment assumes that the position of the preset detection area 5005 is adjusted to an appropriate position as the detection region, but the controller 225 may directly set an appropriate position as the detection region.

In the detection region set by the controller 225, radiation irradiation is detected, and the controller 225 controls imaging based on the dose of radiation entering the detection region. For example, the controller 225 may acquire the integration value of the dose of radiation entering the detection region. Then, when the integration value exceeds a predetermined threshold, the controller 225 may supply, to the radiation generation apparatus 1004, a signal to stop radiation irradiation. In this case, the controller 225 may supply, to the control apparatus 1002, a signal to stop radiation irradiation based on information of the integration value, and in response to this signal, the control apparatus 1002 may supply, to the radiation generation apparatus 1004, a signal to stop radiation irradiation. Furthermore, for example, the controller 225 may transmit, to the control apparatus 1002, the information of the dose of radiation entering the detection region, and the control apparatus 1002 may supply, based on the received dose information, a signal to stop radiation irradiation to the radiation generation apparatus 1004.

In this embodiment, in accordance with the part 5006 to be imaged of the subject 1011 and the rotation angle, the controller 225 sets the detection region at a position away from the side 5011 by the predetermined distance for imaging of the part 5006 to be imaged. This makes the position of the detection area 5005 to be used as the radiation detection region coincide with the part 5006 to be imaged of the subject 1011 positioned with respect to the platform (gantry) 5004 regardless of the rotation angle of the imaging region 100 when viewed from the subject 1011. This can suppress the positional deviation between the radiation detection region and the part 5006 to be imaged of the subject 1011, thereby suppressing degradation of the detection accuracy of radiation irradiation. That is, the radiation imaging apparatus 1001 that properly detects radiation irradiation on the imaging region 100 regardless of the rotation angle of the imaging region 100 with respect to the subject 1011 can be implemented.

Figure 6:
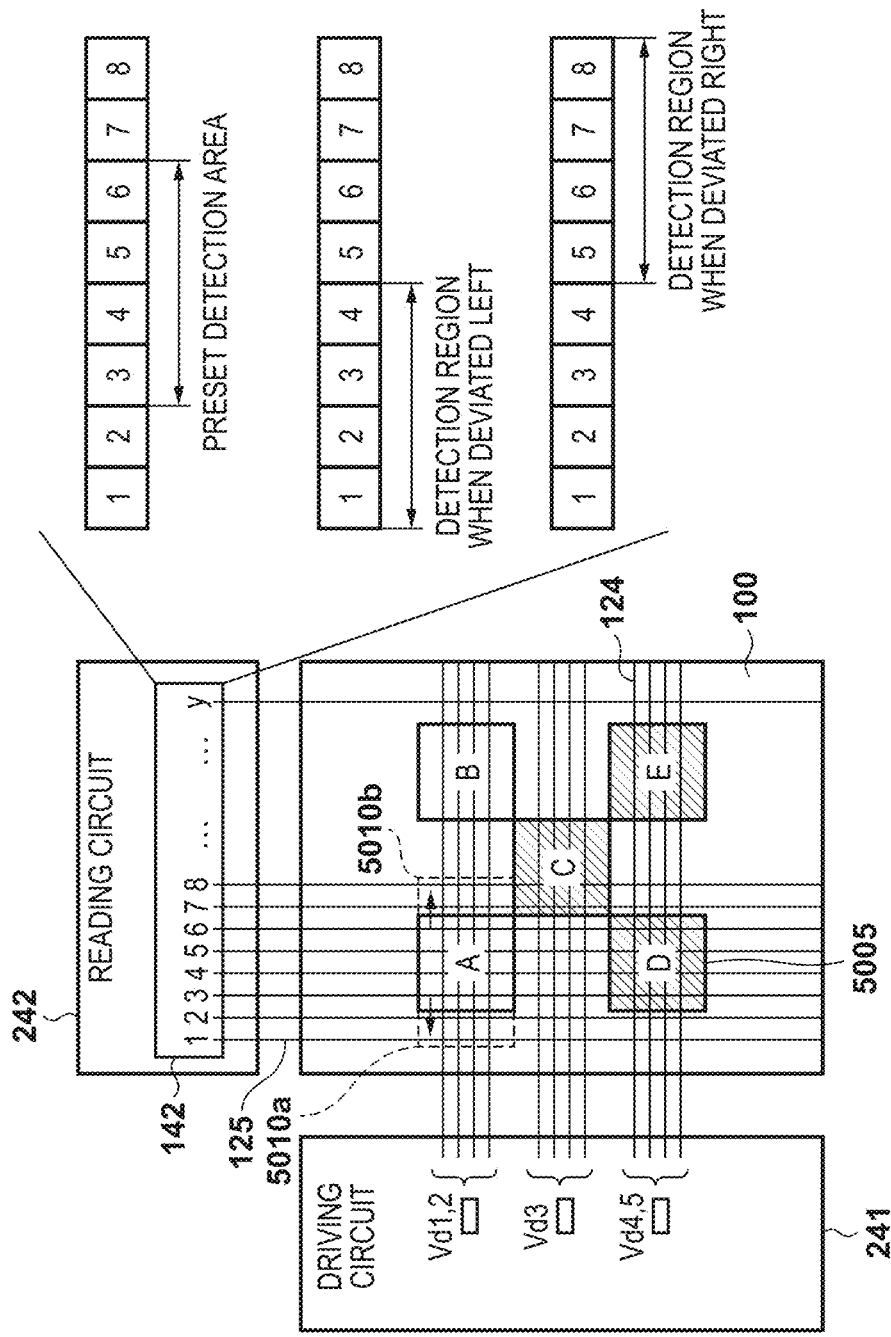
FIG. 6 is a view for explaining a method of setting a detection region of the radiation imaging apparatus shown in FIG. 1.

As described above, in the imaging region 100, the plurality of detection elements 121 for detecting incident radiation are arranged. The controller 225 detects incident radiation using the detection element 121 arranged in the detection area 5005 to be used as the detection region among the plurality of detection elements 121. FIG. 6 is a view for explaining a method of adjusting the detection area 5005 to be used as the radiation detection region in the horizontal direction with respect to the driving lines 124. When adjusting the detection region in the horizontal direction, the position of the detection region may be adjusted by changing the range of the signals of the detection elements 121 read out by the reading circuit 242, which is to be used to detect radiation irradiation.

For example, assume that as the preset detection area A, the signals output from the detection elements 121 via detection signal lines 125-3 to 125-6 of the detection signal lines 125 connected to the detector 142 are used. When moving the detection area A in the horizontal direction to a left position 5010a, the range to be used to detect radiation irradiation is changed to the signals output from the detection elements 121 via the detection signal lines 125 with small numbers after a hyphen such as detection signal lines 125-1 to 125-4. When moving the detection area A in the horizontal direction to a right position 5010b, the range to be used to detect radiation irradiation is changed to the signals output from the detection elements 121 via the detection signal lines 125 with large numbers after a hyphen such as detection signal lines 125-5 to 125-8. This can adjust the radiation detection region to an appropriate position with respect to the preset detection area A. As described above, the controller 225 controls imaging based on the signals output from the detection elements 121 arranged in the detection region (the detection elements 121 set as the detection region) among the plurality of detection elements 121. On the other hand, the controller 225 need not use, for control of imaging, the signals output from the detection elements 121 which are not arranged in the detection region, among the plurality of detection elements 121.

Furthermore, the range of the detection signal lines 125 to be used to detect radiation irradiation may be changed on both the left and right sides, thereby enlarging or reducing the size of the radiation detection region. For example, for the preset detection area A, the signals output from the detection elements 121 via the detection signal lines 125-2 to 125-7 are set as the range to be used to detect radiation irradiation, thereby making it possible to enlarge the detection region in the horizontal direction. Conversely, for the preset detection area A, the signals output from the detection elements 121 via the detection signal lines 125-4 and 125-5 are set as the range to be used to detect radiation irradiation, thereby making it possible to reduce the detection region in the horizontal direction.

Figure 7:
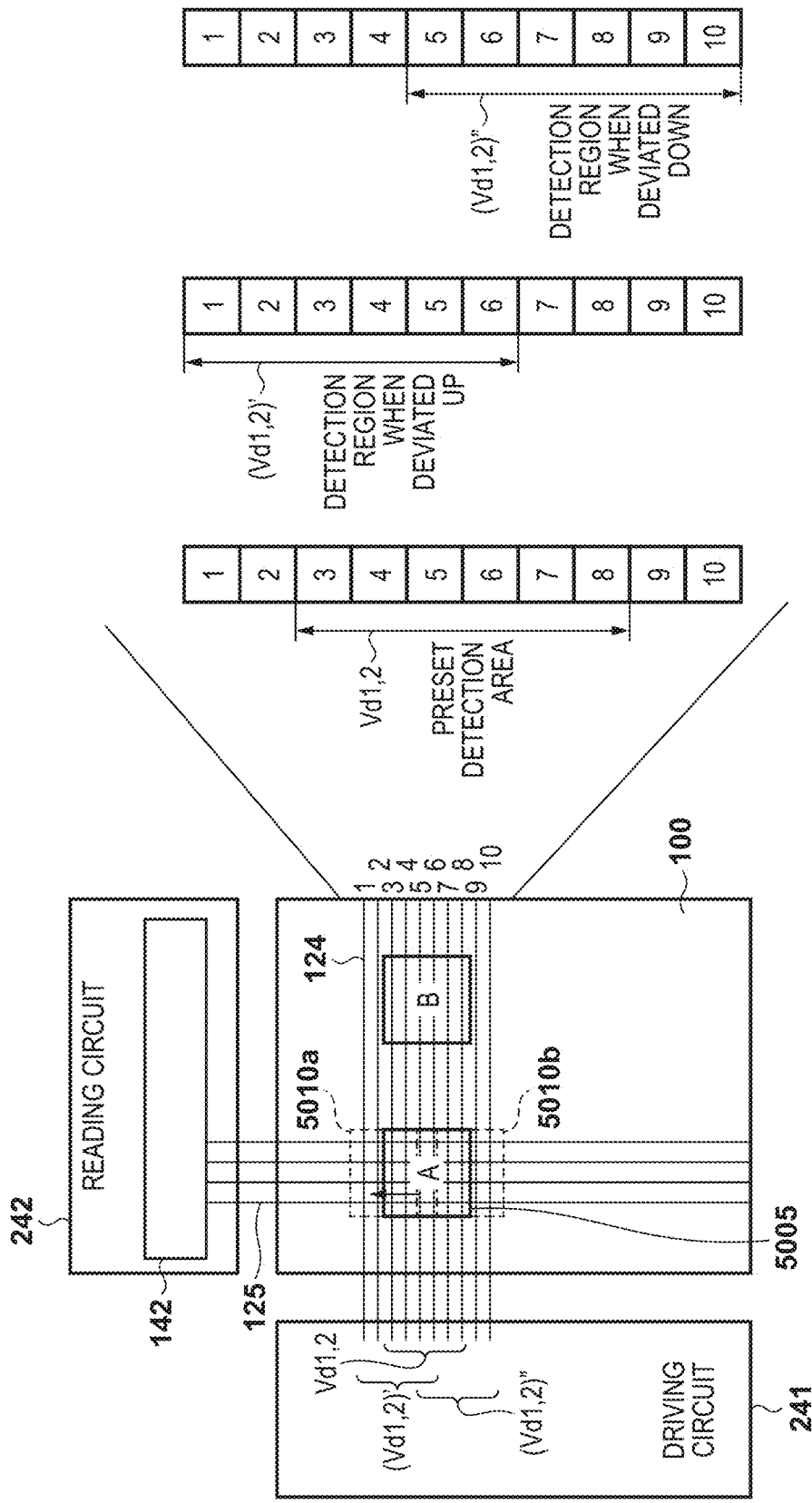
FIG. 7 is a view for explaining a method of setting a detection region of the radiation imaging apparatus shown in FIG. 1.

FIG. 7 is a view for explaining a method of adjusting the detection area 5005 to be used as the radiation detection region in the vertical direction with respect to the driving lines 124. If the detection region is adjusted in the vertical direction, the position of the detection region may be adjusted by changing the driving lines 124 driven by the driving circuit 241.

For example, as the preset detection area A, the signals output from the detection elements 121 by driving driving lines 124-3 to 124-8 among the driving lines 124 connected to the driving circuit 241 are used. If the detection area A is vertically moved to the upper position 5010a, the range to be used to detect radiation irradiation is changed to the signals output from the detection elements 121 by driving the driving lines 124 with small numbers after a hyphen such as driving lines 124-1 to 124-6. If the detection area A is vertically moved to the lower position 5010b, the range to be used to detect radiation irradiation is changed to the signals output from the detection elements 121 by driving the driving lines 124 with large numbers after a hyphen such as driving lines 124-5 to 124-10. This can adjust the radiation detection region to the appropriate position with respect to the preset detection area A. In this way, the controller 225 controls imaging by causing the detection elements 121 arranged in the detection region (set as the detection region), among the plurality of detection elements 121, to output the signals. On the other hand, the controller 225 may not need to cause the detection elements 121, which are not arranged in the detection region, among the plurality of detection elements 121, to output the signals.

Furthermore, it is also possible to enlarge or reduce the size of the radiation detection region by changing, on both the upper and lower sides, the range of the driving lines 124 driven when detecting radiation irradiation. For example, for the preset detection area A, the signals output from the detection elements 121 by driving the driving lines 124-2 to 124-9 are set as the range to be used to detect radiation irradiation. This can enlarge the detection region in the vertical direction. Conversely, for the preset detection area A, the signals output from the detection elements 121 by driving the driving lines 124-4 and 124-5 are set as the range to be used to detect radiation irradiation. This can reduce the detection region in the vertical direction.

By combining the adjustment operations of the preset detection area 5005 in the horizontal and vertical directions, it is possible to change the range to be used as the detection region in the oblique direction. Furthermore, the shape of the detection area 5005 (detection region) is not limited to the square shown in FIGS. 5 to 7. The shape of the detection area 5005 (detection region) may be a rectangle, polygon, or substantially circle, instead of the square. The shape of the imaging region is not limited to the rectangle shown in FIGS. 5 to 7, and may be a square or the like. Furthermore, the arrangement of the driving circuit 241 is not limited to the arrangement in which the driving circuit 241 is connected to the long side of the imaging region 100, as shown in FIGS. 5 to 7, and the driving circuit 241 may be connected to the short side. In this case, the reading circuit 242 may be connected to the long side of the imaging region 100.

Figure 8:
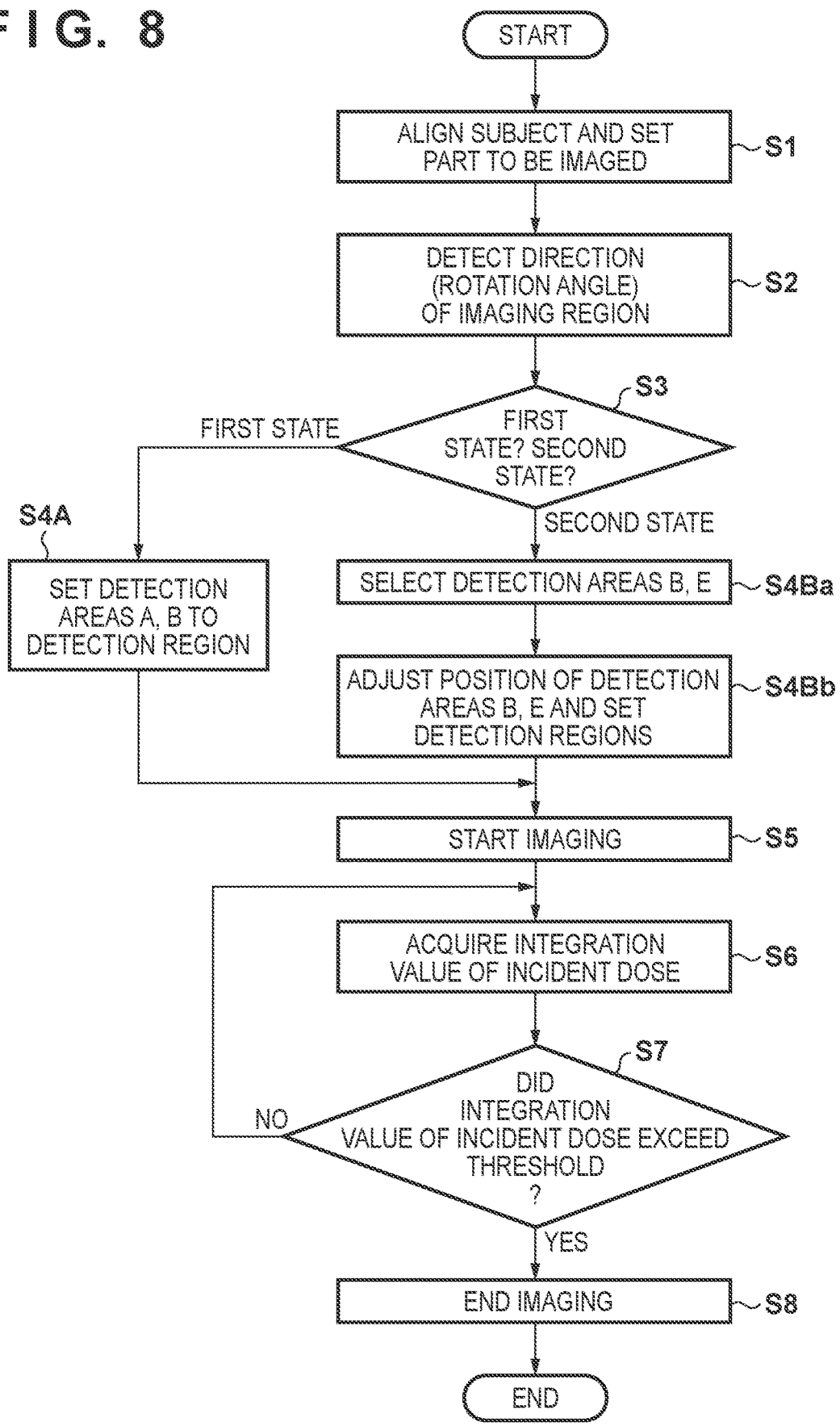
FIG. 8 is a flowchart in imaging in the standing position by the radiation imaging apparatus shown in FIG. 1.

FIG. 8 is a flowchart illustrating the operation procedure of the controller 225 (control apparatus 1002) according to this embodiment. First, the user sets the radiation imaging apparatus 1001 on the platform (gantry) 5004 for imaging in the standing position, and aligns the subject 1011 and the platform (gantry) 5004. This arranges the imaging region 100 to face the subject 1011. Furthermore, the user uses the control apparatus 1002 as an input device, and sets the chest as the part 5006 to be imaged of the subject 1011 (S1).

Next, the controller 225 (control apparatus 1002) causes the rotation detector 5003 to detect the rotation angle of the reference portion of the imaging region 100 about the axis in the normal direction of the imaging region 100 with respect to the reference direction of the subject 1011. Since the radiation imaging apparatus 1001 is stored in the platform (gantry) 5004 for imaging in the standing position and the chest is set as the part to be imaged, the rotation detector 5003 detects the rotation angle of the side 5001 with respect to the direction toward the head of the subject 1011, and transmits the direction of the imaging region 100 to the controller 225 (control apparatus 1002) (S2).

Upon receiving the information of the rotation angle from the rotation detector 5003, the controller 225 (control apparatus 1002) sets the detection region for detecting radiation irradiation in accordance with the rotation angle and the part 5006 to be imaged of the subject 1011. First, the controller 225 (control apparatus 1002) determines the state of the relationship between the imaging region 100 and the subject 1011 (S3). After that, the controller 225 (control apparatus 1002) decides the side located in the same direction as the reference direction of the subject 1011 among the plurality of sides defining the outer edge of the imaging region 100.

Next, the detection region is set at a position away from the decided side by a predetermined distance for imaging of the part 5006 to be imaged.

More specifically, assume that the controller 225 (control apparatus 1002) determines the first state based on the part 5006 to be imaged and the rotation angle detected by the rotation detector 5003. In this case, in accordance with the chest as the part 5006 to be imaged, the controller 225 (control apparatus 1002) selects, as the detection regions, the detection areas A and B close to the side 5011 as the upper side of the imaging region 100 when viewed from the subject 1011 (S4A). In the first state, since the detection areas A and B are arranged at a position away from the side 5011 by the predetermined distance 5501 for imaging of the chest, the position of the detection areas A and B need not be adjusted.

Alternatively, assume that the controller 225 (control apparatus 1002) determines the second state based on the part 5006 to be imaged and the rotation angle detected by the rotation detector 5003. In this case, in accordance with the chest as the part 5006 to be imaged, the controller 225 (control apparatus 1002) selects, as the detection regions, the detection areas B and E close to the side 5011 as the upper side of the imaging region 100 when viewed from the subject 1011 (S4Ba). In the second state, the detection areas B and E are arranged at not a position away from the side 5011 by the predetermined distance 5501 for imaging of the chest but a position away from the side 5011 by the distance 5502. Thus, the controller 225 (control apparatus 1002) adjusts the position of the detection areas B and E to the position 5010 away from the side 5011 by the distance 5501, thereby setting the detection regions (S4Bb).

The controller 225 of the radiation imaging apparatus 1001 may enable radiation detection in the detection area 5005 set as the detection region, and disable radiation detection in the detection area 5005 which has not been set. For example, consider a case in which the detection areas A and B are set as the detection regions. In this case, the controller 225 of the radiation imaging apparatus 1001 may enable accumulation of charges of the detection elements 121 in the detection areas A and B, and disable accumulation of charges of the detection elements 121 in the remaining detection areas C to E. Furthermore, the controller 225 of the radiation imaging apparatus 1001 may control not to drive, by the driving circuit 241, the detection elements 121 in the detection areas C to E other than the detection areas A and B. The controller 225 of the radiation imaging apparatus 1001 may control not to perform digital conversion, by the AD converter 146 of the reading circuit 242, for the signals from the detection elements 121 in the detection areas C to E other than the detection areas A and B. In other words, the AD converter 146 may AD-convert the signals output from the detection elements 121 arranged in the detection regions among the plurality of detection elements 121 to supply them to the controller 225, and need not AD-convert the signals output from the detection elements 121 which are not arranged in the detection regions, among the plurality of detection elements 121. The controller 225 of the radiation imaging apparatus 1001 may control not to perform processing, by the signal processor 224, for the signals from the detection elements 121 in the detection areas C to E other than the detection areas A and B. In this way, by various methods of disabling radiation detection in the detection areas other than the detection areas 5005 set as the detection regions, the controller 225 (control apparatus 1002) can perform integration of the arrival dose and an application stop request at high speed.

Next, in response to the pressing of the irradiation switch 1006 by the user, the controller 225 (control apparatus 1002) transmits an irradiation control signal (application request) to the radiation generation apparatus 1004. In response to the irradiation control signal, the radiation generation apparatus 1004 causes the radiation source 1003 to start radiation irradiation, thereby starting imaging (S5). During radiation irradiation (imaging), the controller 225 (control apparatus 1002) acquires information of the dose of radiation entering the detection area 5005 set as the detection region, and acquires the integration value of the incident dose (S6).

During radiation irradiation (imaging), the controller 225 (control apparatus 1002) determines, for example, whether the integration value of the dose of radiation entering the detection area 5005 set as the detection region exceeds a predetermined threshold (S7). If the integration value of the dose of radiation does not exceed the predetermined threshold, the controller 225 (control apparatus 1002) repeats steps S6 and S7; otherwise, the controller 225 (control apparatus 1002) supplies an application stop request signal to the radiation generation apparatus 1004 to stop radiation irradiation. In response to the application stop request signal, the radiation generation apparatus 1004 causes the radiation source 1003 to stop generation of radiation. This ends imaging (S8). When there exist the plurality of detection areas 5005 set as the detection regions, if the integration value of the dose of radiation obtained by one of the plurality of detection areas 5005 exceeds the predetermined threshold, the controller 225 (control apparatus 1002) may supply the application stop request signal. Alternatively, if the integration value of the doses of radiation obtained by all of the plurality of detection areas 5005 exceeds the predetermined threshold, the controller 225 (control apparatus 1002) may supply the application stop request signal. For example, when the user sets imaging conditions, these conditions are set.

With the above processing, the incident dose of the detection area 5005 set as the detection region in accordance with the part 5006 to be imaged of the subject 1011 is monitored, thereby making it possible to stop radiation irradiation at an appropriate timing. This can prevent extra radiation irradiation on the subject 1011, and acquire a radiation image with satisfactory quality by an appropriate irradiation amount.

The above-described example has explained the arrangement in which the controller 225 of the radiation imaging apparatus 1001 sets the detection region in accordance with the part to be imaged of the subject 1011 and the rotation angle detected by the rotation detector 5003. The present invention, however, is not limited to this. For example, the controller 225 causes all the detection elements 121 or all the set detection areas 5005 to output signals. The controller 225 or the control apparatus 1002 may select an appropriate signal from the signals in accordance with the part to be imaged of the subject 1011 and the rotation angle detected by the rotation detector 5003, and monitor radiation irradiation.

OTHER EMBODIMENTS

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s)

and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2021-087189, filed May 24, 2021, which is hereby incorporated by reference herein in its entirety.

What is claimed is:

1. A radiation imaging apparatus, comprising:
an imaging region in which a plurality of pixels configured to generate signals to acquire a radiation image corresponding to incident radiation are arranged;
a controller configured to set a detection region as a region to be used to detect the radiation in addition to acquisition of the radiation image in the imaging region; and
a rotation detector, wherein
when the imaging region is arranged to face a subject, the rotation detector is configured to detect a rotation angle of a reference portion of the imaging region about an axis in a normal direction of the imaging region with respect to a reference direction of the subject,
the controller is configured to decide, in accordance with a part to be imaged of the subject and the rotation angle, a side located in the same direction as the reference direction of the subject among a plurality of sides defining an outer edge of the imaging region,
the controller is configured to set by adjusting a position of the detection region so that a distance from the side to the detection region is equal to a predetermined distance for imaging of the part to be imaged, and
the controller is configured to control imaging based on a dose of the radiation entering the adjusted detection region.

2. The apparatus according to claim 1, wherein a plurality of detection areas for detecting incident radiation are preset in the imaging region,
the controller is configured to select a detection area to be used as the detection region from the plurality of detection areas in accordance with the part to be imaged and the rotation angle, and
the controller is configured to adjust a position of the selected detection area so that a distance from the side to the selected detection area is equal to the predetermined distance.

3. The apparatus according to claim 2, wherein the controller is configured to select, as the detection area to be used as the detection region, a detection area closest to the side among the plurality of detection areas.

4. The apparatus according to claim 2, wherein each of the plurality of detection areas is rectangular.

5. The apparatus according to claim 1, wherein the rotation detector is configured to detect the rotation angle by detecting a direction of the reference portion with respect to a vertical direction.

6. The apparatus according to claim 5, wherein the rotation detector comprises an acceleration sensor.

7. The apparatus according to claim 1, wherein the rotation detector is configured to detect the rotation angle by detecting a detection object fixed to a gantry to which the radiation imaging apparatus is attached.

8. The apparatus according to claim 7, wherein the detection object comprises a magnetic material, and
the rotation detector comprises a magnetic sensor.

9. The apparatus according to claim 1, wherein a plurality of detection elements configured to detect incident radiation are arranged in the imaging region, and
the controller is configured to detect the incident radiation using the detection element which is arranged in the detection region, among the plurality of detection elements.

10. The apparatus according to claim 9, wherein the controller is configured to cause the detection element which is arranged in the detection region, among the plurality of detection elements, to output a signal, and is configured to not cause the detection element which is not arranged in the detection region, among the plurality of detection elements, to output a signal.

11. The apparatus according to claim 9, wherein the controller is configured to control imaging based on the signal output from the detection element which is arranged in the detection region, among the plurality of detection elements, and is configured to not use, for control of imaging, the signal output from the detection element which is not arranged in the detection region, among the plurality of detection elements.

12. The apparatus according to claim 9, further comprising an AD converter configured to AD-convert a signal output from the imaging region, wherein
the AD converter is configured to AD-convert the signal output from the detection element which is arranged in the detection region, among the plurality of detection elements, to supply the signal to the controller, and is configured to not AD-convert the signal output from the detection element which is not arranged in the detection region, among the plurality of detection elements.

13. The apparatus according to claim 9, wherein a part of the plurality of pixels each function as one of the plurality of detection elements.

14. The apparatus according to claim 9, wherein in addition to the plurality of pixels, the plurality of detection elements are arranged.

15. The apparatus according to claim 1, wherein the reference direction is a direction toward a head of the subject.

16. The apparatus according to claim 1, wherein the part to be imaged is a chest of the subject.

17. A radiation imaging system, comprising:
the radiation imaging apparatus according to claim 1; and
a radiation generation apparatus configured to irradiate the radiation imaging apparatus with radiation, wherein
a controller is configured to acquire an integration value of a dose of radiation entering a detection region, and is configured to supply a signal to stop the radiation irradiation to the radiation generation apparatus when the integration value exceeds a predetermined threshold.

18. A control apparatus for controlling a radiation imaging apparatus, comprising:
an imaging region in which a plurality of pixels configured to generate signals to acquire a radiation image corresponding to incident radiation are arranged;
a rotation detector; and
a radiation generation apparatus configured to irradiate the radiation imaging apparatus with the radiation, wherein
when the imaging region is arranged to face a subject, the rotation detector is configured to detect a rotation angle of a reference portion of the imaging region about an axis in a normal direction of the imaging region with respect to a reference direction of the subject,
the control apparatus is configured to control the radiation generation apparatus based on a dose of the radiation detected in a detection region as a region to be used to detect the radiation in addition to acquisition of the radiation image in the imaging region,
the control apparatus is configured to decide, in accordance with a part to be imaged of the subject and the rotation angle, a side located in the same direction as the reference direction of the subject among a plurality of sides defining an outer edge of the imaging region, and
the control apparatus is configured to set by adjusting a position of the detection region so that a distance from the side to the detection region is equal to a predetermined distance for imaging of the part to be imaged.

19. A control method of a radiation imaging apparatus comprising an imaging region in which a plurality of pixels configured to generate signals to acquire a radiation image corresponding to incident radiation are arranged, and a rotation detector, the method comprising the steps of:
arranging the imaging region to face a subject;
causing the rotation detector to detect a rotation angle of a reference portion of the imaging region about an axis in a normal direction of the imaging region with respect to a reference direction of the subject;
setting a detection region as a region to be used to detect the radiation in addition to acquisition of the radiation image in the imaging region; and
controlling imaging based on a dose of the radiation entering the detection region, wherein
a side located in the same direction as the reference direction of the subject is decided among a plurality of sides defining an outer edge of the imaging region in accordance with a part to be imaged of the subject and the rotation angle, and
the detection region is set by adjusting a position for the detection region so that a distance from the side to the detection region is equal to a predetermined distance for imaging of the part to be imaged.

20. A non-transitory computer-readable storage medium storing a program for causing a computer to execute a control method of a radiation imaging apparatus comprising an imaging region in which a plurality of pixels configured to generate signals to acquire a radiation image corresponding to incident radiation are arranged, and a rotation detector, the method comprising the steps of:
arranging the imaging region to face a subject;
causing the rotation detector to detect a rotation angle of a reference portion of the imaging region about an axis in a normal direction of the imaging region with respect to a reference direction of the subject;
setting a detection region as a region to be used to detect the radiation in addition to acquisition of the radiation image in the imaging region; and
controlling imaging based on a dose of the radiation entering the detection region, wherein
a side located in the same direction as the reference direction of the subject is decided among a plurality of sides defining an outer edge of the imaging region in accordance with a part to be imaged of the subject and the rotation angle, and
the detection region is set by adjusting a position for the detection region so that a distance from the side to the detection region is equal to a predetermined distance for imaging of the part to be imaged.

* * * * *